United States Patent [19]

Jaeger

[11] Patent Number: 5,707,197
[45] Date of Patent: Jan. 13, 1998

[54] APPARATUS FOR DISPENSING SUCCESSIVE ZONES OF A DISPOSABLE STRIP

[75] Inventor: Gérard Jaeger, Blonay, Switzerland

[73] Assignee: Asulab S.A., Bienne, Switzerland

[21] Appl. No.: 639,902

[22] Filed: Apr. 29, 1996

[30] Foreign Application Priority Data

May 2, 1995 [FR] France .................................. 95 05223

[51] Int. Cl.$^6$ ................................................. G01N 37/00
[52] U.S. Cl. ............................... 414/14; 604/407; 221/18
[58] Field of Search .......................... 30/40.1; 221/18, 221/19, 20, 152; 414/14; 604/403, 407

[56] References Cited

U.S. PATENT DOCUMENTS

| | | |
|---|---|---|
| 4,196,515 | 4/1980 | Sugiyama . |
| 5,047,044 | 9/1991 | Smith et al. . |
| 5,460,294 | 10/1995 | Williams ................................ 221/152 |

FOREIGN PATENT DOCUMENTS

| | | |
|---|---|---|
| 2710412 | 3/1995 | France . |
| 2710414 | 3/1995 | France . |
| 8904481 | 5/1989 | WIPO . |

*Primary Examiner*—Karen B. Merritt
*Assistant Examiner*—Gregory A. Morse
*Attorney, Agent, or Firm*—Sughrue, Mion, Zinn, Macpeak & Seas, PLLC

[57] ABSTRACT

This apparatus operates with disposable strips which are inserted therein by a user. It comprises a circulation passage (29) for the strips (34) wherein a cursor (35) is able to slide, each strip being able to be coupled to the cursor. A mechansim is provided so that the cursor (35) is able to move in the passage (29) only if it is coupled to a strip. Moreover, the cursor (35) remains blocked in the vicinity of the opening (28) of the circulation passage when no strips (34) are present. This invention can be applied in particular to objects dispensing devices such as medical tablets or to blood sugar level measuring devices.

7 Claims, 6 Drawing Sheets

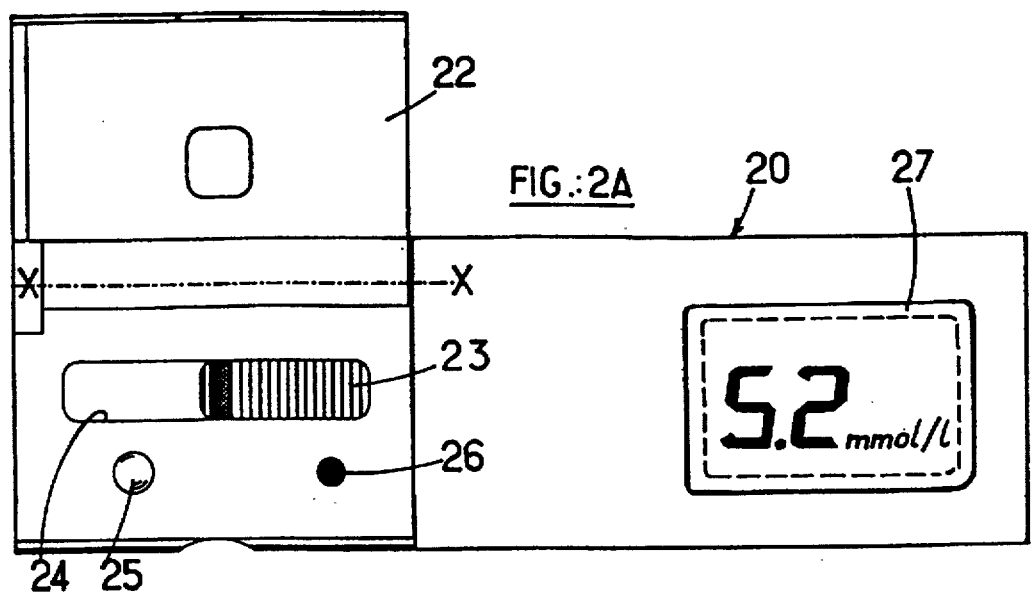
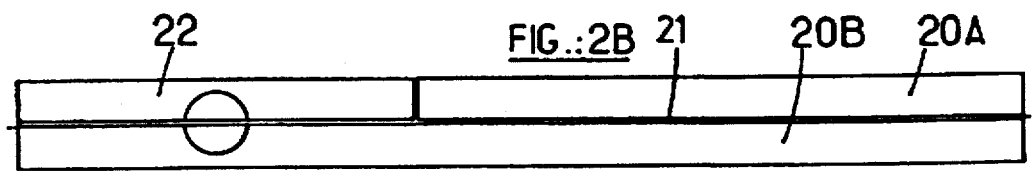
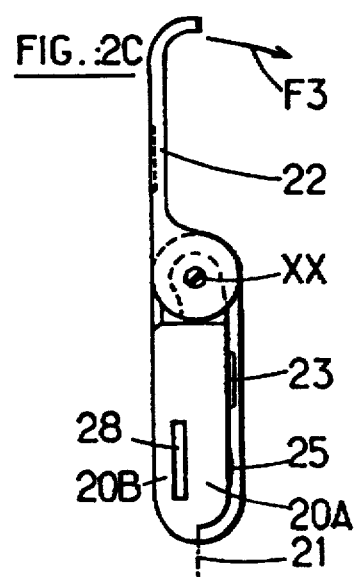

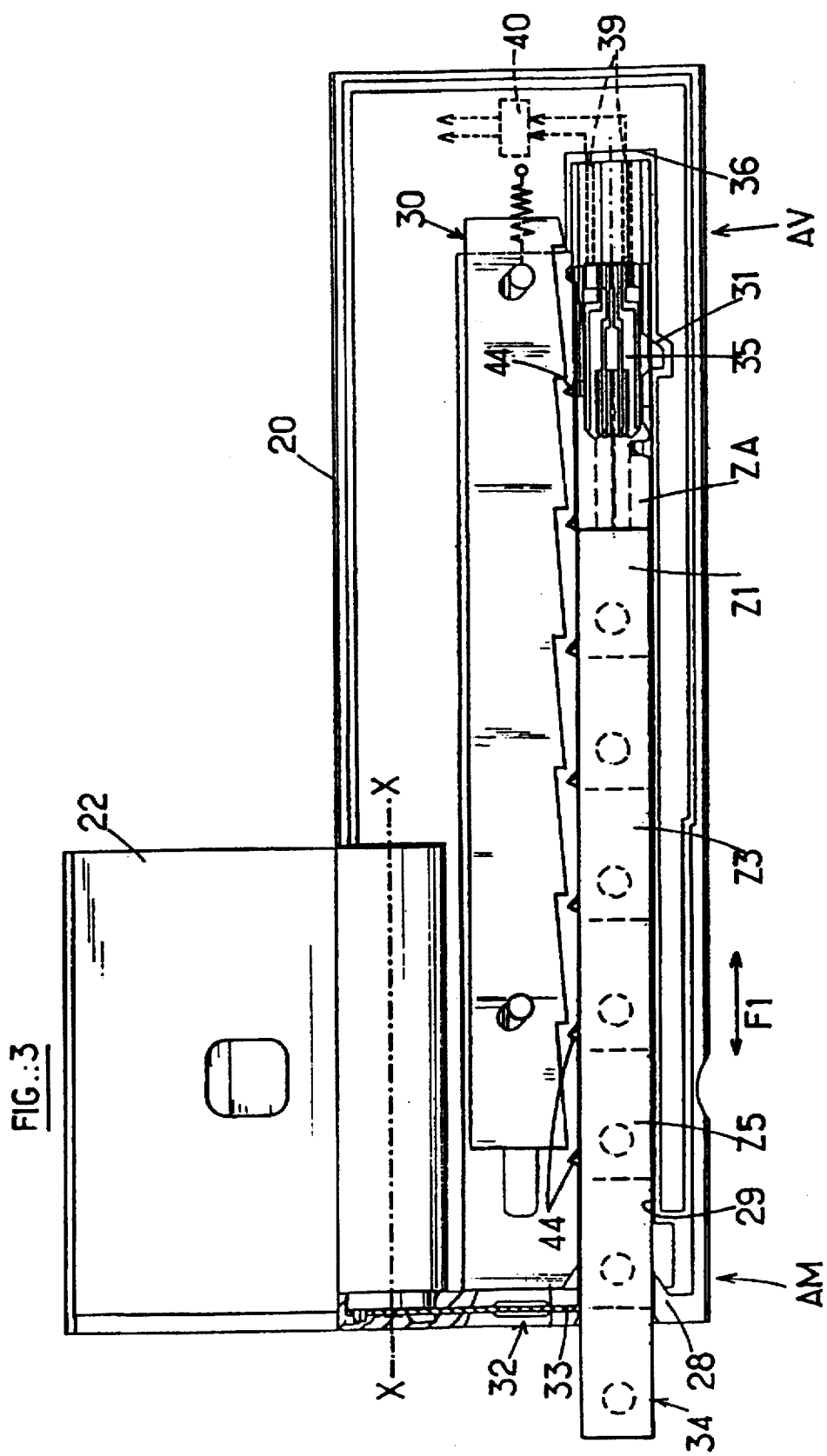

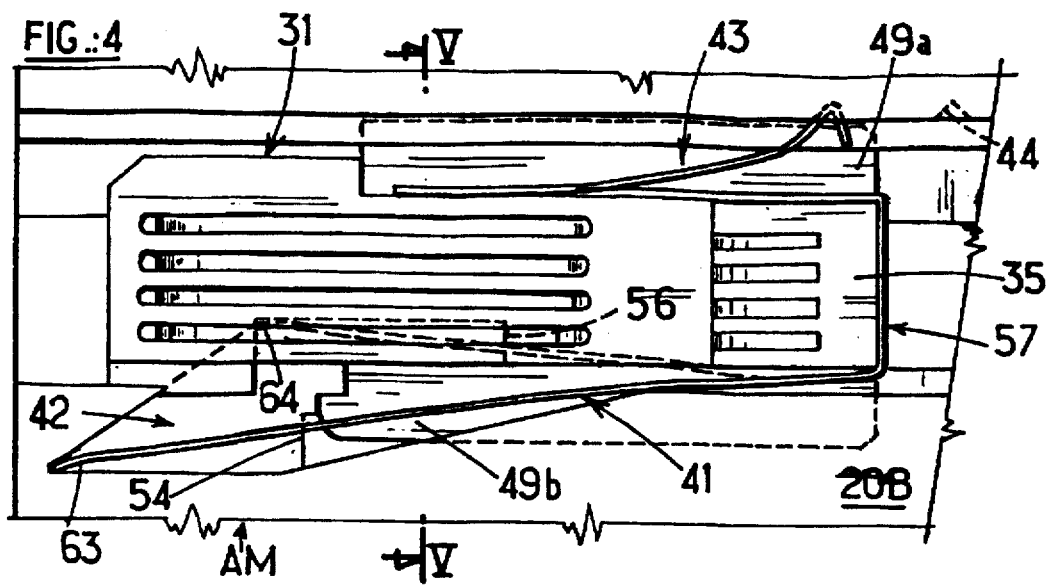
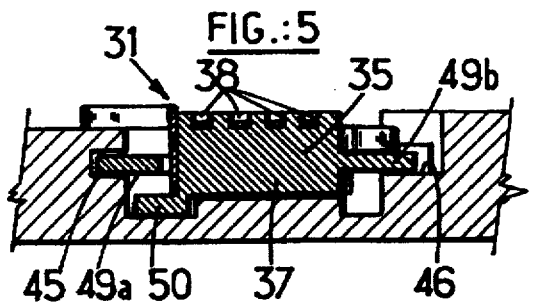
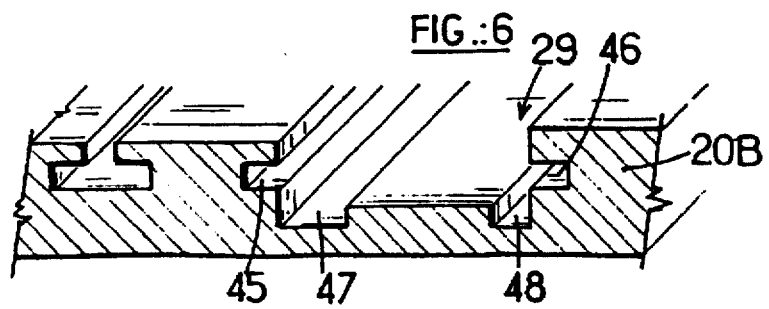

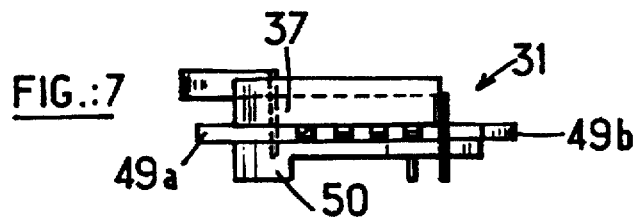
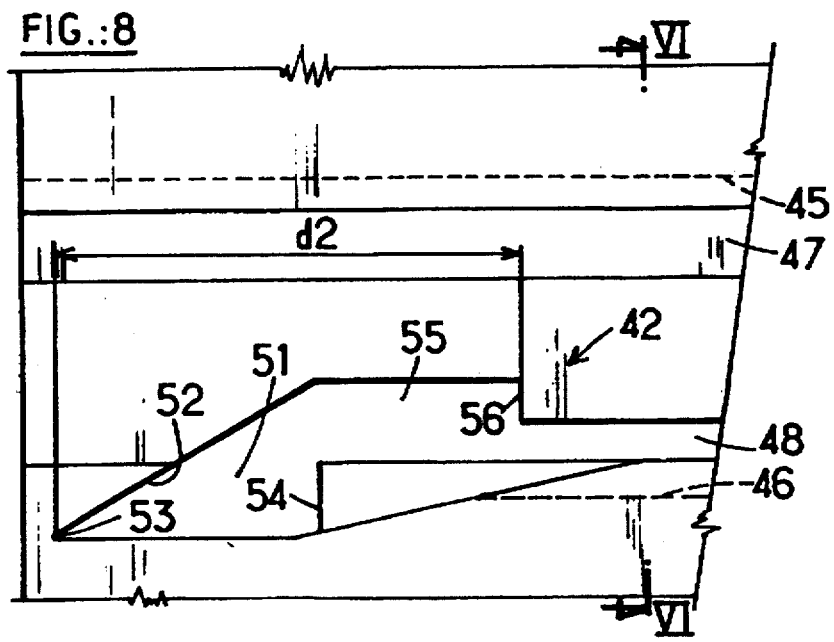
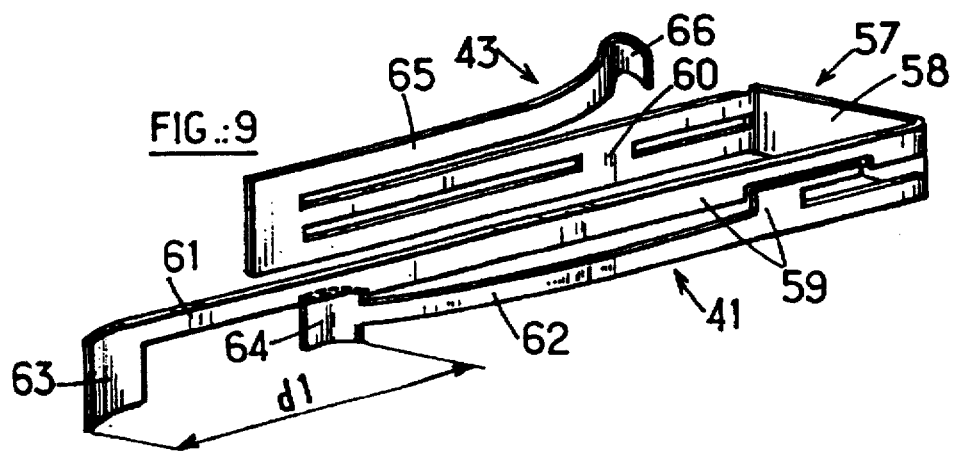

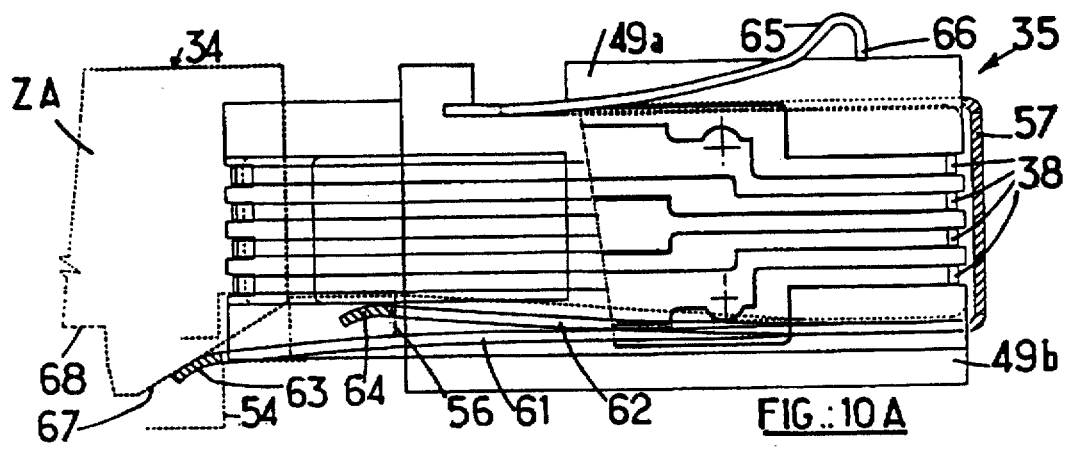
FIG.:10A
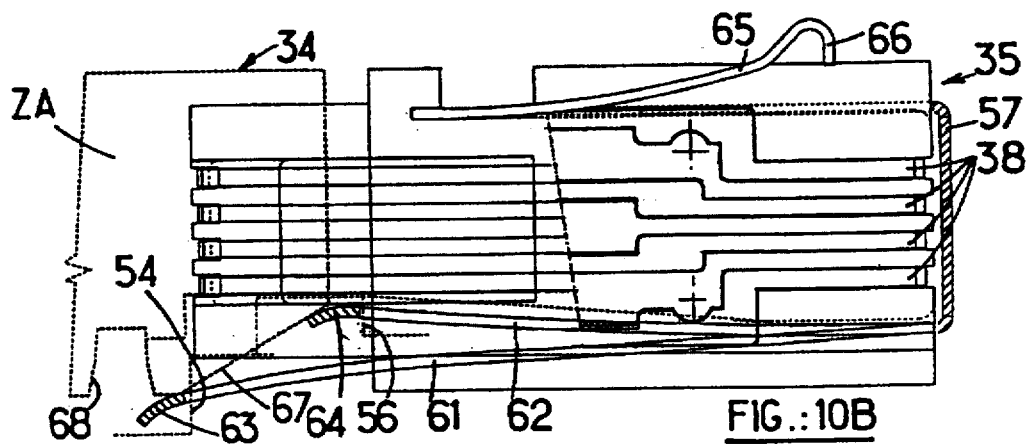
FIG.:10B
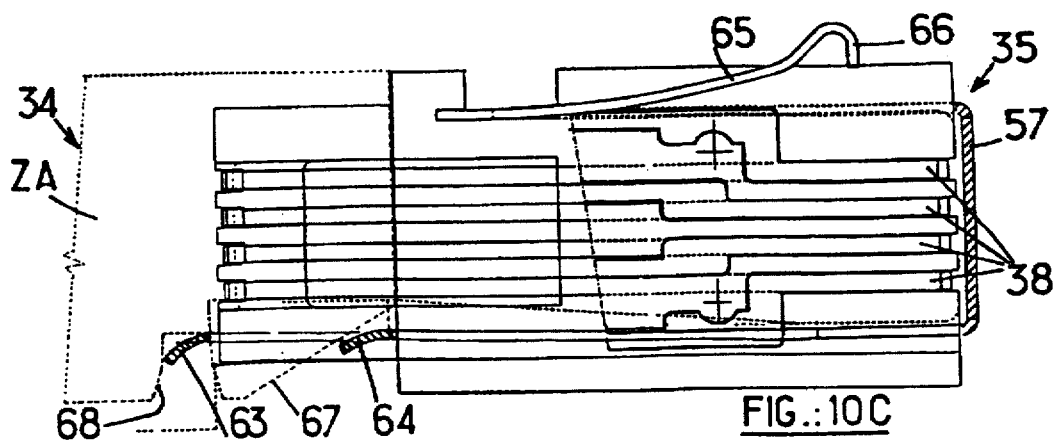
FIG.:10C

APPARATUS FOR DISPENSING SUCCESSIVE ZONES OF A DISPOSABLE STRIP

The present invention relates to a dispensing apparatus requiring the use of disposable elements in the shape of a strip to operate, each of these strips comprising in the longitudinal direction several successive utilisation zones intended to be detached from the strip after their use.

More particularly, the invention concerns an apparatus of this type forming a measuring device enabling a parameter of a substance deposited on successive zones of a strip forming a disposable measuring sensor, also called a multizone sensor, to be measured.

A measuring device of this type may advantageously be used for measuring blood sugar levels, for use by diabetics. Different aspects of such a device have been disclosed in several French patents filed in the name of the applicant and amongst which one may cite patent FR 92 01331 as regards the electrochemical measuring method used, patent application FR 93 11316 as regards a cutting device enabling the used measuring zones to be detached from the disposable strip, FR 93 11317 as regards an electrical connection device enabling the sensor strip to be connected to an electronic measuring circuit intended to elaborate the result of the measurement in a form intelligible to a user, and finally FR 93 11319 which concerns more specifically a device for ejecting the last section of the sensor strip, when all the measuring zones have been used.

FIG. 1 of the attached drawings shows a measuring device in which one finds, in summary form, an embodiment example of the improvements which were the subject of the aforementioned patent applications, it being understood that in order to find a detailed description of them, one may refer to the texts of said patent applications.

Thus, the measuring device comprises a case 1, of a general elongated shape and of such a size that it can easily be held in the palm of an adult's hand. This case defines a circulation passage 2 longitudinally oriented in case 1 and intended for the circulation of a sensor strip 3 (double arrow F1) and a cursor 4. The latter is responsible for transmitting the electric signal coming from sensor strip 3 to electric lines 5 which extend along passage 2. These lines are in turn connected to an electronic circuit 6 intended to process this electric signal in a suitable manner to make it intelligible to a user by means of a display device which is also provided in case 1.

In the example of FIG. 1, sensor strip 3 is specifically adapted for measuring blood sugar levels. A detailed description of a strip of this type can be found in the first patent application cited above. One need only keep in mind here that it comprises several measuring zones, seven in this case referenced Z1 to Z7 of which zone Z7 shown in dotted lines is assumed already to have been used and detached from strip 3.

It will also be noted that the sensor strip comprises for each of zones Z1 to Z7 a forward feed catch 7 on one of its longitudinal edges and for each of the zones except zone Z7 a positioning notch 8 situated on the other edge of the strip.

Forward feed catches 7 co-operate with a longitudinal forward feed mechanism 9 of strip 3 along its passage 2. The latter comprises a control button (not visible in FIG. 1) mounted so as to slide longitudinally in the case, that is to say as seen in FIG. 1, above passage 2.

The control button co-operates with a rotating latch 10 guided on two studs 11 and 12 which are attached to a bar 13. The latter is coupled to the control button and mounted so as to slide in case 1 in the direction of arrow F1 against the action of a return spring 14 fixed to case 1. Rotating latch 10 is held in a non active position (shown in FIG. 1) by a leaf spring 15 and comprises a central nose 16 intended to co-operate with forward feed catches 7 of sensor strip 3.

Thus, it is understood that when the control button is activated back and forth, the sensor strip moves forward the length of a measuring zone of the strip, the forward feed mechanism causing latch 10 to rotate in a reciprocating manner (along arrow F2) to first of all push the strip out of the passage by one step and then to return to the inactive position as shown by disengaging itself from the strip.

The device also comprises a cover 17 rotatably mounted on the case around an axis X—X and mechanically coupled to a cutting mechanism 18 enabling the disposable zone of the strip which has just been used to be cut, by a simple closing movement of cover 17.

It is also to be noted that cursor 4 slides freely in passage 2 and is pushed backwards when disposable sensor strip 3 is inserted. The latter is mechanically coupled during this insertion when cursor 4 abuts the bottom of passage 2. The cursor carries for this purpose an resilient coupling member which yields to the insertion force exerted on strip 3 by the user, in order to latch onto this strip as soon as the insertion force is released.

Operating tests of the measuring device which has just been described have shown that it functions satisfactorily and without difficulty as long as the strips are entirely used and have a sufficient initial length to be able to be cut by the cursor, when the latter is situated at the bottom of the passage.

Consequently, strips which are partially used or which, when manufactured, have a shorter length cannot be used, given that, in such case, the coupling with the cursor cannot be carried out.

An aim of the invention is to provide a solution to the problem cited above.

The invention thus concerns a dispensing apparatus requiring the use of disposable elements having the shape of strips to operate, each of these strips comprising in the longitudinal direction several successive utilisation zones intended to be detached from the strip after their use, said apparatus comprising:

a case defining a circulation passage for said strips, said passage having, taking account of the direction in which said strips are introduced, an upstream end and a downstream end, a forward feed mechanism for bringing said strip out of the circulation passage in accordance with a step by step movement after its introduction into the latter by a user, a sliding unit mounted so as to move in said passage, operationally coupled to said forward feed mechanism and intended to be coupled to the corresponding end of said strip when it is introduced by the user, and coupling means carried by said sliding unit and arranged so as to assure the coupling between the latter and said strip, said apparatus being characterised in that said case also defines stop forming means situated at the upstream end of said passage, and in that it also comprises blocking means arranged for, in co-operation with said stop forming means, assuring the blocking of said sliding unit in a position situated upstream of said passage in the absence of a strip in the latter and for releasing said sliding unit to move in said passage after the coupling of the downstream end of said strip with said sliding unit.

As a result of these features, the sliding unit is blocked at the upstream opening of the circulation passage, a position to which it can always be returned by the forward feed mechanism and from which it can only move upstream in the passage when it is coupled to a disposable strip.

Other features and advantages of the invention will appear during the following description, which is given solely by way of example and made with reference to the attached drawings in which:

FIG. 1, already described, is a schematical plane view, partially cut away, of a dispensing apparatus according to the aforecited patent applications;

FIGS. 2A, 2B and 2C are three exterior views, according to three orthogonal planes, of a dispensing apparatus according to the invention;

FIG. 3 is a plane view of a dispensing apparatus according to the invention, the upper part of its case being assumed to have been removed;

FIG. 4 is a larger scale plane view of the cursor of the apparatus according to the invention, to illustrate its essential features;

FIG. 5 is a cross-sectional view taken along the broken line V—V of FIG. 4;

FIG. 6 is an end view of the guiding passage of the disposable strips;

FIG. 7 is an end view of a cursor intended to move in the guiding passage;

FIG. 8 shows in plane the beginning of the guiding passage and the cam and stop forming means which are arranged in it;

FIG. 9 shows a perspective view of the resilient blocking and coupling means forming part of the apparatus according to the invention; and FIGS. 10A, 10B and 10C are schematical views similar to FIG. 4 and showing schematically the operation of the apparatus according to the invention.

Figure 1:
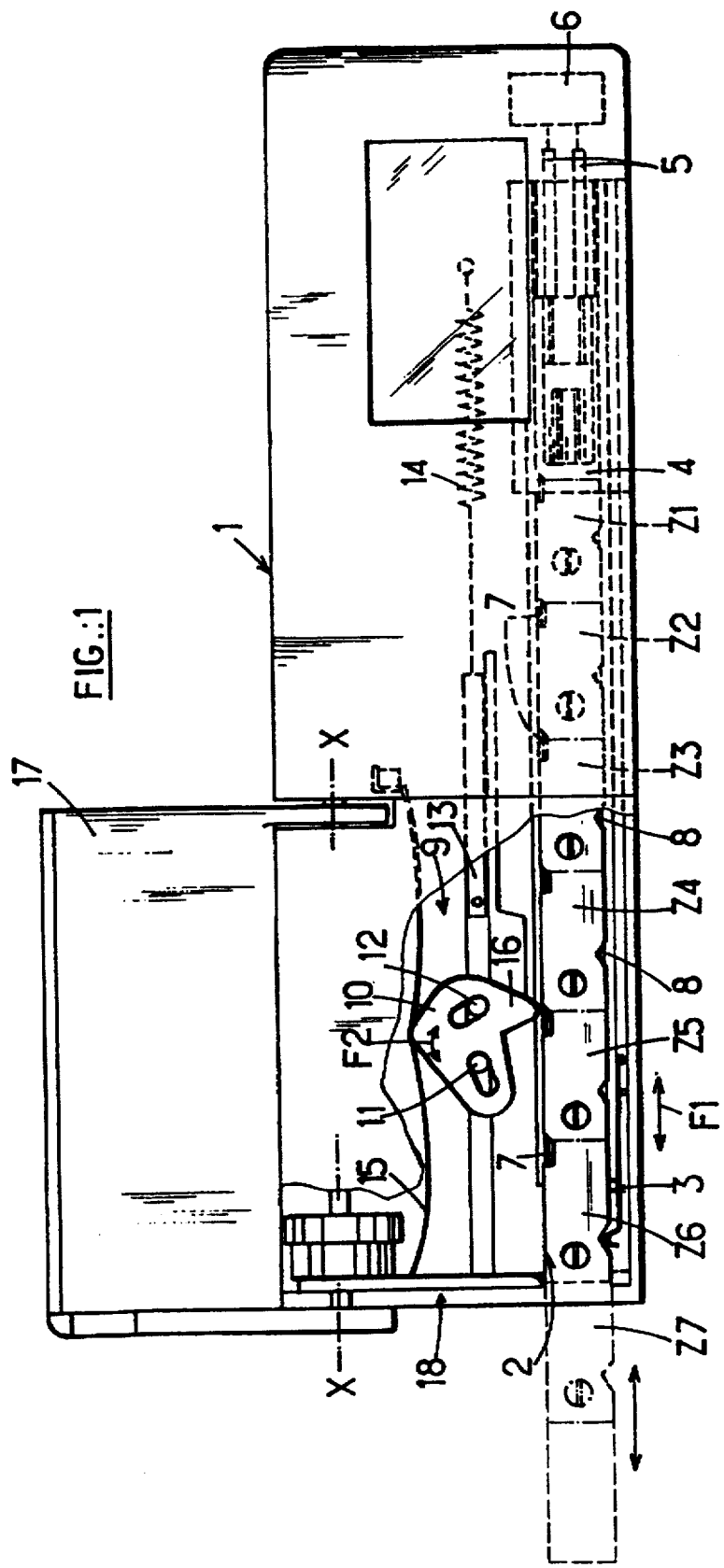

The drawings show a preferred embodiment of the dispensing apparatus according to the invention in its application to a device enabling blood sugar levels to be measured for use by diabetics, for example. However, the invention is not limited to this specific application. Indeed, it may be implemented in all sorts of other applications in which it is desirable to use disposable strips on which adjacent zones define a specific utilisation area, these zones after having been used being able, or even having to be (for medical reasons for example) removed from the strip to make room for a following zone. For example, in the medical field, an apparatus of this type could be used for dispensing a series of medical tablets or pills required, in accordance with the dosage prescribed by the doctor, to be taken in a strict order defined in advance. However, the invention is not limited either to applications in the medical field.

The dispensing apparatus according to the invention shown in the drawings comprises a case 20 made of two half shells 20A and 20B, preferably in a moulded plastic material, and assembled to each other along a parting line 21. In the application described, case 20 has an elongated shape and dimensions such that it can easily be held in the palm of an adult's hand.

The apparatus comprises a cover 22 extending over part of its length and which is hinged onto case 20 about a longitudinal axis X—X and which may be folded back onto case 20 by activating it in the direction of the arrow F3 (FIG. 2C).

In FIGS. 2A and 2C, cover 22 has been shown in an open position, so that one can see a button 23 sliding in a guide 24 arranged in upper half shell 20A of case 20. A small magnifying lens 25 enables a part of the disposable strip (not shown here) which is slid inside the apparatus to be observed. A push button 26 is intended to recall previously taken measurements stored in the memory of the apparatus, for display on a display 27 also used to enable the results of the measurement which has just been made to be read immediately.

It is to be noted that the apparatus is switched on as soon as button 23 is activated and its power supply (preferably an incorporated battery) is switched off after the lapse of a predetermined period of time (60 seconds for example) defined from the moment when any manipulation of the apparatus by the user has ceased.

From the side of cover 22, on the lateral narrow edge of case 20, the apparatus has an opening 28 which is the mouth of a circulation passage 29 (FIG. 3) of the disposable strips.

FIG. 3 shows the dispensing apparatus according to the invention with upper half shell 20A having been removed. Consequently, several operating units can be observed, and in particular:

- a forward feed mechanism 30 which will not be described in detail here, but in relation to which it need only be kept in mind that it enables a disposable strip to be fed step by step into passage 29 via the repeated action of sliding button 23;
- a sliding unit 31, which is intended to be coupled to a disposable strip and slides into passage 29;
- a cutting unit 32 situated along the lateral narrow edge of the apparatus and comprising a blade 33 mounted so as to slide in a perpendicular direction to axis X—X; and
- a disposable strip 34 having seven measuring zones Z1 to Z7 and a zone ZA forming a leader zone of the strip and enabling it to be coupled to sliding unit 31.

Reference will now be made to FIGS. 4 to 9 in order to describe more specifically the features of the present invention which refer to sliding unit 31 and the manner in which the latter is coupled to a disposable strip 34.

Sliding unit 31 comprises a cursor 35 capable of circulating in passage 29 which is blocked at its end 36 opposite opening 28. This end will be referred to below as "downstream end" AV in view of the movement of introduction of strip 34 into passage 29. Of course, the opposite end, close to opening 28 will be called "upstream end" AM. These terms will also be used for the disposable strip, its downstream end thus being situated close to leader zone ZA.

Cursor 35 comprises a cursor body 37 carrying electric transmission means 38 for assuring the pick up of electric signals from strip 34 and the transmission of these signals to contact strips 39 which run along the upper wall of passage 29 (as seen in the drawings). According to an alternative embodiment a flexible flat cable which extends into passage 29 could also be provided for this purpose.

Contact strips 39 are connected to an electronic processing circuit 40 which is in turn connected to display 27 (FIG. 2A).

Body 37 also carries resilient blocking and coupling means 41 which are designed in conformity with the features of the present invention. These means 41 cooperate with cam and stop forming means 42 which are in one piece with lower half shell 20B of case 20.

Body 37 further comprises driving and positioning means 43 intended to co-operate with forward feed means 30 and with indexing catches 44 which are provided along passage 29 and respectively define the measuring positions of strip 34.

In FIGS. 6 and 8 one sees that guiding passage 29 has two lateral longitudinal grooves 45, 46 and two longitudinal grooves 47 and 48 arranged in its bottom. Body 37 (FIG. 7) is of a general parallelepipedal shape from which two lateral ribs 49a and 49b protrude, respectively fitting into lateral grooves 45 and 46 and a lower rib 50 which fits into groove 47 provided in the bottom of passage 29.

FIG. 8 shows cam and stop forming means 42 which are moulded into lower half shell 20B. More precisely, next to opening 28, the external wall of groove 48 has a notch 51 whose upstream wall 52 (seen in the direction of introduction of strip 34) is arranged slantwise. This wall acts as a cam and the tip 53 arranged thus in this notch 51 constitutes a stop. Notch 51 also defines a downstream stop 54 oriented perpendicular to the longitudinal direction of groove 48.

Opposite, the lower lateral wall of groove 48 also has a notch 55 whose upstream wall extends slantwise wall 52 and whose downstream wall is also oriented perpendicular to groove 48 to form a stop 56.

Resilient blocking and coupling means 41 and driving and positioning means 43 are preferably made in a same spring plate 57 (FIG. 4 and 9). The latter has a U-shape and may for example be compound filled with the plastic material when cursor 35 is moulded. The central branch 58 of the U is applied against the downstream face of cursor 35 while its lateral branches 59 and 60 extend towards opening 28 of passage 29 running respectively along the lateral sides of cursor 35.

Branch 59 is slit longitudinally to form two superposed springs 61, 62 of unequal lengths which each terminate at its free end in a finger blade 63, 64 bent outwards. The other branch 60 is also slit longitudinally on the one hand to enable the plastic material to be attached during moulding and on the other hand to define a spring 65 which extends downstream and terminates in a hook 66.

The resilience of springs 61, 62 and 65 is determined in such a way that of springs 61 and 62 draws their respective finger blade 63, 64 inwards, while that of spring 65 draws hook 66 outwards.

One sees in particular in FIGS. 3 and 10A to 10C that leader zone ZA of the disposable strip has at its forward end, on the one hand a sloping edge 67 forming a cam, and on the other hand, situated slightly towards the rear, a lateral coupling notch 68. It will be noted that the disposable strip is thus asymmetrical vis-a-vis its longitudinal axis so that the sloping edge in particular forms a polarising slot which allows the user only one way to introduce it into the apparatus.

FIGS. 4, 10A, 10B and 10C show different positions of the members of the apparatus, respectively before and during the introduction of a disposable strip 34 into the apparatus.

First of all in FIG. 4, leader zone ZA of a preceding disposable strip has been ejected from passage 29 and, having been brought upstream during the use of this strip, cursor 35 is situated upstream in passage 29. In this position, this cursor is prevented from moving downstream and, of course, also from moving out of passage 29. Indeed, finger blade 64 is in position in notch 55 of the case, stop 56 opposing any movement of the cursor downstream. Furthermore, finger blade 63 of spring 61 is pushed back outwards on ramp 52, the tip or stop 53 opposing any movement upstream.

It should be noted that in this configuration, cursor 35 preferably retains a certain freedom of movement in passage 29, the distance d1 between the active upstream edge 63a (FIG. 9) of finger blade 63 and the downstream active edge 64a of finger blade 64 being slightly less than the distance d2 (FIG. 8) which separates stop 53 from stop 56.

In FIG. 10A, disposable strip 34 has just been presented before opening 28 (FIG. 3) and its leader zone ZA has already been slightly introduced into it. By pushing on the strip, the user will cause a backward movement of cursor 35 via the contact of ramp 67 with finger blade 63. This movement continues until the finger blade abuts stop 56.

By continuing to exert an introduction force on strip 34, the user will overcome the resistance of electric transmission means 38 which until then have been resisting their own elastic deformation. The strip may then continue to be introduced and to be coupled to cursor 35, while ramp 67 begins to push finger blade 64 of spring 62 outwards (FIG. 10B). At about the same time, finger blade 63 reaches the end of ramp 67 of leader zone ZA.

As soon as finger blade 64 is released from stop 56, it may then enter passage 29 upstream. It is to be noted that finger blade 64 must be disengaged from stop 56 before finger blade 63 falls into notch 68.

However, cursor 35 cannot leave as long as finger blade 63 abuts the lateral edge of leader zone ZA, given the presence of stop 54. But as soon as finger blade 63 can be introduced into notch 68 of leader zone ZA, the cursor may be moved pushed by strip 34. Indeed, notch 68 is sufficiently deep for finger blade 63 to move at the level of groove 48 of passage 29.

Consequently, as shown in FIG. 10C, the two finger blades are then situated in a position in which they can circulate in groove 48, as a result of which, cursor 35 is then free to move downstream. Disposable strip 34 is attached to the cursor until said contact is brought back upstream again via forward feed mechanism 31.

One thus sees that the two springs 61 and 62 form resilient members which, when disposable strip 34 is introduced, take over from each other to block temporarily the movement of cursor 35 in passage 29 until the joint coupling of the cursor and the disposable strip takes place. Consequently, cursor 35 cannot move backwards without being coupled to the disposable strip. In other words, the cursor can only be in the upstream position of FIG. 10A, when there is no disposable strip or part of the latter in the apparatus.

It is to be noted furthermore that the resilient members or springs 61 and 62 release the disposable strip as soon as the cursor is in the upstream position, since in these circumstances, finger blade 63 is pushed back out of notch 68 of the disposable strip.

What is claimed is:

1. A dispensing apparatus requiring the use of disposable elements having the shape of strips to operate, each of these strips comprising in the longitudinal direction several successive utilisation zones intended to be detached from the strip after their use, said apparatus comprising:

a case defining a circulation passage for said strips, said passage having, taking account of the direction in which said strips are introduced, an upstream end and a downstream end, a forward feed mechanism for bringing said strip out of the circulation passage in accordance with a step by step movement after its introduction into the latter by a user, a sliding unit mounted so as to move in said passage, operationally coupled to said forward feed mechanism and intended to be coupled to the corresponding end of said strip when it is introduced by the user, and coupling means carried by said sliding unit and arranged so as to assure the coupling between the latter and said strip, said case also defining stop forming means situated at the upstream end of said passage, and in that it comprises in addition blocking means arranged to assure, in cooperation with said stop forming means, the blocking of said sliding unit in an upstream position of said passage in the absence of a strip in the latter and to release said sliding unit to move in said passage when the downstream end of said strip is coupled to said sliding unit.

2. An apparatus according to claim 1, wherein said blocking means are arranged to only allow the release of said sliding unit when the coupling between said strip and said unit is completed.

3. An apparatus according to claim 2 wherein:

said blocking means comprise first and second resilient members;

said stop forming means comprise first and second stops intended to co-operate respectively with said first and second resilient members so as to oppose movement of said sliding unit from the upstream end towards the downstream end, until said coupling between said strip and said sliding unit has been completed;

said first resilient member also defines a coupling member of said coupling means intended to engage with said strip when the latter is coupled with said sliding unit; and when said strip is introduced, said first resilient member cannot move aside from said first stop to be coupled to said strip, before the second resilient member is released from said second stop.

4. An apparatus according to claim 3, wherein said resilient members are leaf springs fixed at one end onto said sliding unit, extending in the direction of the circulation passage and carrying at their other end a finger blade intended to co-operate with said corresponding stop.

5. An apparatus according to claim 4, wherein the finger blades of said leaf springs are arranged to cooperate with an edge in the shape of a ramp of each of said strips.

6. An apparatus according to claim 4, wherein the finger blade of said first resilient member is arranged to engage in a notch provided in the lateral edge of each of said strips to assure the fixing of the strip to said sliding unit.

7. An apparatus according to claim 4, wherein said stop forming means also comprise an additional stop and a ramp situated at the upstream end of said passage and intended to co-operate with said finger blade of said first resilient member to oppose the removal of said sliding unit from said passage.

* * * * *